US005830723A

United States Patent [19]
Foster et al.

[11] Patent Number: 5,830,723
[45] Date of Patent: *Nov. 3, 1998

[54] METHOD FOR IMMORTALIZING CHICKEN CELLS

[75] Inventors: Douglas N. Foster, Roseville; James A. Farris, Lino Lakes; Linda K. Foster, Roseville, all of Minn.

[73] Assignee: Regents of the University of Minnesota, Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 696,376

[22] Filed: Aug. 13, 1996

[51] Int. Cl.$^6$ .............................. C12N 5/10; C12N 7/02; C12N 15/63; C12N 15/86

[52] U.S. Cl. .................................. 435/172.2; 435/172.3; 435/235.1; 435/325; 435/349; 435/373

[58] Field of Search ............................ 435/172.2, 172.3, 435/325, 273, 235.1, 349

[56] References Cited

FOREIGN PATENT DOCUMENTS

| 2 634 784 | 2/1990 | France . |
|---|---|---|
| 41 42 452 | 6/1993 | Germany . |
| WO 95/02041 | 1/1995 | WIPO . |
| WO 95/31567 | 11/1995 | WIPO . |

OTHER PUBLICATIONS

Farris et al., Poultry Science 74(Suppl. 1):68, abstract 203 (1995).
C.F. Boerkoel et al., "A New Defective Retroviral Vector System Based on the Bryan Strain of Rous Sacoma Virus", *Virology*, 195(2) 669–679 (1993).
Boyer et al., "Sequence and biological activity of chicken snoN cDNA clones", *Oncogene*, 8 457–466 (1993).
L.B. Crittenden et al., "Host Gene Control of Endogenous Avian Leukosis Virus Production", *Virology*, 57 128–138 (1974).
L. Curatolo et al., "Culture Conditions Induce the Appearance of Immortalized $C_3H$ Mouse Cell Lines", *In Vitro*, 20 597–601 (1984).
A.B. De Leo et al., "Detection of a transformation–related antigen in chemically induced sarcomas and other transformed cells of the mouse", *Proc. Natl. Acad. Sci. USA*, 76 2420–2424 (1979).
D. Eliyahu et al., "Participation of p53 cellular tumour antigen in transformation of normal embryonic cells", *Nature*, 312 646–649 (1984).
L. Fernando et al. "Cloning and expression of an avian metallothionein–encoding gene", *Gene*, 81 177–183 (1989).
Federspiel et al., "Effects of the gag Region on Genome Stability: Avian Retroviral Vectors That Contain Sequences from the Bryan Strain of Rous Sarcoma Virus[1]", *Virology*, 203(2) 211–220 (1994).
Givol et al., "Overexpression of human p21$^{waf1/cip1}$ arrests the growth of chicken embryo fibroblasts transformed by individual oncogenes", *Oncogene*, 11(12) 2609–2618 (1995).

Givol et al., "Bcl–2 Expressed Using a Retroviral Vector Is Localized Primarily in the Nuclear Membrane and the Endoplasmic Reticulum of Chicken Embryo Fibroblasts[1]", *Cell Growth & Differentiation*, 5(4) 419–429 (1994).
C. Gorman et al., "High Efficiency DNA–Mediated Transformation of Primated Cells", *Science*, 221 555–553 (1983).
Hamburger et al., "Soft–Agar Cloning of Cells From Patients With Lymphoma", *Prog. Clin. Biol. Res., Cloning of Human Tumor Stem Cells*, 43–52 (1980).
L.Hayflick, "The Limited In Vitro Lifetime of Human Diploid Cell Strains", *Exp. Cell Res.*, 37 614–636 (1965).
J.R. Jenkins et al., "The cellular oncogene p53 can be activated by mutagenesis", *Nature*, 317 816–818 (1985).
M. Kastan et al., "Participation of ⊔Protein in the Cellular Response to DNA Damage", *Cancer Research*, 51 6304–6311 (1991).
B. Kressner et al., "Use an Image Analysis System to Count Colonies in Stem Cell Assays of Human Tumors", *Prog. Clin. Biol. Res., Cloning of Human Tumor Stem Cells*, 48 179–193 (1980).
R.L. Meek et al., "Establishment of Mouse Embryo Cells In Vitro", *Exp. Cell Res.*, 107 277–284 (1977).
W.E. Mercer et al., "Role of the p53 Protein in Cell Proliferation as Studied by Microinjection of Monoclonal Antibodies", *Molecular and Cellular Biology*, 4 276–281 (1984).
D. Michalovitz et al., "Conditional Inhibition of Transformation and of Cell Proliferation by a Temperature–Sensitive Mutant of p53", *Cell*, 52 671–680 (1990).
L. Parada et al., "Cooperation between gene encoding p53 tumour antigen and ras in cellular transformation", *Nature*, 312 649–651 (1984).
Pereira–Smith et al., "Genetic analysis of indefinite division in human cells: Identification of four complementation groups", *Proc. Natl. Acad. Sci. USA*, 85 6042–6046 (1988).
Pereira–Smith et al., "Hybrids From Fusion of Normal Human T Lymphocytes With Immortal Human Cells Exhibit Limited Life Span", *J. Cell Physiol.*, 144 546–549 (1990).
J. Pontén, "The Relationship Between In Vitro Transformation and Tumor Formation In Vivo", *Biochim. Biophys. Acta.*, 458 397–422 (1976).
J. Pontén, "Spontaneous and Virus Induced Transformation in Cell Culture", *Virology Monographs*, 8 1–3(1971).
B. Rovinski et al., "Immortalization of rat embryo fibroblasts by the cellular p53 oncogene", *Oncogene*, 2 445–452 (1988).

(List continued on next page.)

*Primary Examiner*—Johnny F. Railey, II
*Attorney, Agent, or Firm*—Mueting, Paasch, & Gebhardt

[57] ABSTRACT

This invention relates to the introduction of p53 under the control of the metallothionein promoter into primary cells to produce immortalized cell lines. The cells are useful as substrates for viral propagation, as contaminant-free sources for recombinant protein production, for recombinant virus production and as cell substrates to support primary cells and improve virus yield during virus propagation.

14 Claims, 2 Drawing Sheets

OTHER PUBLICATIONS

S. Salmon, "Morphologic Studies of Tumor Colonies", *Prog. Clin. Biol. Res., Cloning of Human Tumor Stem Cells,* 48 135–151 (1980).

J.R. Smith et al., "Genetic and Molecular Studies of Cellular Immortalization", *Adv. Cancer Research,* 54 63–77 (1990).

Smith et al. "Replicative Senescence: Implications for in Vivo Aging and Tumor Suppression", *Science,* 273 63–67 (1996).

T. Soussi et al., "Nucleotide sequence of a cDNA encoding the chicken p53 nuclear oncoprotein", *Nucleic Acids Research,* 16 11383–11384 (1988).

G. Todaro et al., "Quantitative Studies of the Growth of Mouse Embryo Cells in Culture and Their Development into Established Lines", *J. Cell Biology,* 17 299–313 (1963).

Cicuttini et al., "Support of Human Cord Blood Progenitor Cells Human Stromal Cell Lines Transformed by $SV_{40}$ Large T Antigen Under the Influence of an Inducible (Metallothionein) Promotor," *Blood,* 80(1), 102–112 (1992).

Jenkins et al., "Cellular immortalization of a cDNA clone encoding the transformation–associated phosphoprotein p53," *Nature,* 312, 651–653 (1984).

McLean, "Improved techniques for immortalizing animal cells,"*Trends in Biotechnology,* 11(6), 232–238 (1993).

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1555 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:1:

```
GAATTCCGAA  CGGCGGCGGC  GGCGGCGGCG  AACGGAGGGG  TGCCCCCCA   GGGACCCCC     60
AACATGGCGG  AGGAGATGGA  ACCATTGCTG  GAACCCACTG  AGGTCTTCAT  GGACCTCTGG   120
AGCATGCTCC  CCTATAGCAT  GCAACAGCTG  CCCCTCCCTG  AGGATCACAG  CAACTGGCAG   180
GAGCTGAGCC  CCCTGGAACC  CAGCGACCCC  CCCCCACCAC  CGCCACCACC  ACCTCTGCCA   240
TTGGCCGCCG  CCGCCCCCCC  CCCATTAAAC  CCCCCACCC   CCCCCGCGC   TGCCCCTCC    300
CCGGTGGTCC  CATCCACGGA  GGATTATGGG  GGGGACTTCG  ACTTCCGGGT  GGGGTTCGTG   360
GAGGCGGGCA  CAGCCAAATC  GGTCACCTGC  ACTTACTCCC  CGGTGCTGAA  TAAGGTCTAT   420
TGCCGCCTGG  CCAAGCCGTG  CCCGGTGCAG  GTGAGGGTGG  GGGTGGCGCC  CCCCCCGGT    480
TCCTCCCTCC  GCGCCGTGGC  CGTCTATAAG  AAATCAGAGC  ACGTGGCCGA  AGTGGTGCGG   540
CGCTGCCCCC  ACCACGAGCG  CTGCGGGGGG  GGCACCGACG  GCCTGGCCCC  CGCACAGCAC   600
CTCATCCGGG  TGGAGGGGAA  CCCCCAGGCG  CGTTACCACG  ACGACGAGAC  CACCAAACGG   660
CACAGCGTCG  TCGTCCCCTA  TGAGCCCCCC  GAGGTGGGCT  CTGACTGTAC  CACGGTGCTG   720
TACAACTTCA  TGTGCAACAG  TTCCTGCATG  GGGGGGATGA  ACCGCCGCCC  CATCCTCACC   780
ATCCTTACAC  TGGAGGGGCC  GGGGGGGCAG  CTGTTGGGGC  GGCGCTGCTT  CGAGGTGCGC   840
GTGTGCGCAT  GTCCGGGGAG  GGACCGCAAG  ATCGAGGAGG  AGAACTTCCG  CAAGAGGGGC   900
GGGGCCGGGG  GCGTGGCTAA  GCGAGCCATG  TCGCCCCCAA  CCGAAGCCCC  CGAGCCCCCC   960
AAGAAGCGCG  TGCTGAACCC  CGACAATGAG  ATATTCTACC  TGCAGGTGCG  CGGGCGCCGC  1020
CGCTATGAGA  TGCTGAAGGA  GATCAATGAG  GCGCTGCAGC  TCGCCGAGGG  GGGGTCCGCA  1080
CCGCGGCCTT  CCAAAGGCCG  CCGTGTGAAG  GTGGAGGGAC  CCCAACCCAG  CTGCGGGAAG  1140
```

```
AAACTGCTGC  AAAAAGGCTC  GGACTGACCA  CGCCCCCTTT  TTCCTTTAGC  CACGCCCCTT    1 2 0 0

TCCCTTCAGG  CCCGGCCCAT  TTCCCTTCAG  CCCCGGCCCC  ATTTCCCTTC  AGCCACGCCC    1 2 6 0

AATTTCCCCT  TTACCACGCC  CCCTTTCCCT  TCAGCCACGC  CCCCTTTCCC  CTTAGCCACT    1 3 2 0

CCCCTTCCCC  CGCGAAAGCC  CCGCCCACCC  CCGCCGTAAC  CACGCCCACG  CTTCCCACCC    1 3 8 0

CCCTCCCAAT  CTGACCACGC  CCCCTTTACG  CCTTAACCAC  GCCCCTCTC   TCCTGGCCCC    1 4 4 0

GCCCCCCTCC  GCTTTGGCCA  TGCGTAAATC  CCCCCCCCG   CCCCCCCCG   GCTCATTTTT    1 5 0 0

AATGCTTTTT  TTGATACAAT  AAAACTTCTT  TTTTACTGA   AAAAAAAGG   AATTC         1 5 5 5
```

( 2 ) INFORMATION FOR SEQ ID NO:2:

( i ) SEQUENCE CHARACTERISTICS:
        ( A ) LENGTH: 626 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:2:

```
CTCTCAGCAC  GGCCCCACGC  TGTGCGCACC  GCCTCGCAGC  GCGGCCCGGG  GGGGTGGCGG     6 0

GGGTGGGAGC  AGCAGTGGCG  CAATGACCCC  TCCGGGTCAC  ATTCCCGCAA  CCGAGCGCAG    1 2 0

AGTGCGTGGC  CGGGAAATTC  CCCCCCCCA   ATTCGCCTTT  CGGCAGCCAA  AGCGGGAGGG    1 8 0

GGGGAGTGAG  GAGGGTCAGG  CACGTTGGGG  TCCGTGCCGT  GTTCTGGCAA  AGTGTCGTGT    2 4 0

TTGGGGGGGG  GGGGGAGCAA  GGAAGGGAGG  CGAGGGGTGA  GGACACAAAG  CAAAAGCGCC    3 0 0

CTAAATCTGT  TGGCACACAT  GGCCATCCCA  CAGCTGTATC  CCCCTGCTTT  GGGGGAACCC    3 6 0

CAACACCAGG  GCTGGCCCCG  CGGTGAGGCT  CCCCCAGGC   AGGGGCACG   GCCGTGACCC    4 2 0

CGCTGAGCAC  GGCACGGCGC  TGCCCCGCCC  CGCTGAGCAC  GGCACGGCAC  GGCACGGCAC    4 8 0

GGCCCCCCGA  GCACGGCTCA  GCACGGCACG  GCGCTCAGCA  CGGCACGGAT  CGGCACCGCC    5 4 0

CCGCCGTGCG  CTGCGCGCAG  CACCACCCCG  GCCCTATAAA  ATACAGGGCG  GGCAGCGGGA    6 0 0

CTCGGGACTG  CTAGAGCCCA  CCCGAG                                           6 2 6
```

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
CGAAGATCTC  TCAGCACGGC  CCCACGCT                                           2 8
```

( 2 ) INFORMATION FOR SEQ ID NO:4:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
CGAAGATCTT  TATTCTCGAG  ATATCGAATT  CTCGGGTGGG  CTCGTAGCAG  T             5 1
```

METHOD FOR IMMORTALIZING CHICKEN CELLS

FIELD OF THE INVENTION

This invention relates to the field of cell immortalization and the use of cells as reservoirs for virus growth and recombinant protein expression. In particular this invention relates to the use of the protein p53 under the control of an inducible promoter to produce immortalized cells.

BACKGROUND OF THE INVENTION

Many avian viruses used for the production of avian and animal vaccines are propagated in embryonated chicken eggs or primary chicken fibroblast cultures. Examples of animal vaccines manufactured using these chicken substrates include Canine Distemper for dogs, Marek's disease vaccines for turkeys, Reovirus, Fowl Pox and Infectious Bursal Disease vaccines for poultry. Primary cell cultures can be highly variable and present a risk of contamination by endogenous viruses, mycoplasmas, and the like. Sources for animal tissues from which the primary cell cultures are derived are often limited and expensive due to the need to maintain animal stocks in a pathogen-free state.

There is a need to develop a reproducible methodology to generate virus-free immortalized avian cell substrates that are suitable for use in the manufacture of animal vaccine products. The availability of well-characterized immortalized (i.e., continuous) cell lines has the benefit of eliminating or reducing the dependence on primary animal tissue cultures which are poorly controlled from a quality standpoint. In the vaccine industry, regulatory requirements for product safety, consistency and potency are driving companies to pursue cell lines as the best alternative to the current practice of using egg-based and primary cell vaccine substrates. Vaccine production companies must have defined consistent cell lines for virus production to meet the regulatory requirements to permit the companies to disseminate their vaccines. Manufacturers of both human and animal vaccine products in both the United States and abroad must demonstrate that their vaccine substrates are free from contaminants. The advent of a reproducible method for generating continuous animal cell lines derived from primary tissues will enable manufacturers of biological products to better control production processes and increase both product safety and consistency while ultimately reducing cost.

SUMMARY OF THE INVENTION

This invention relates to a method for transforming cells and cells produced by introducing nucleic acid encoding p53 under the control of the metallothionein promoter into the cells and selecting cells with immortalized characteristics.

In one aspect of this invention a method is disclosed for transforming primary non-rodent cells comprising the steps of: positioning nucleic acid encoding p53 under the control of a metallothionein promoter in a gene vector capable of directing expression of p53; introducing the gene vector into primary non-rodent cells; and selecting foci of cells with population doubling times of about 0.6 to about 1.5 population doublings per day, wherein the cells are reverse-transcriptase negative and are non-tumorigenic. In one embodiment the primary non-rodent cells are avian-derived and in another embodiment the primary non-rodent cells are human-derived. The primary cells used in this invention can be from any number of tissues and in a preferred embodiment the cells are obtained from skin tissue, breast muscle tissue and/or heart muscle tissue.

In another aspect of this invention, cells are disclosed. These cells are immortalized fibroblasts containing a gene vector capable of expressing p53 under the control of the metallothionein promoter. In one embodiment the cells are avian derived.

This invention also relates to a method for growing virus comprising the steps of: contacting at least one infectious virus particle with at least one cell of an immortalized cell culture, wherein the cells of the culture contain a gene vector capable of directing expression of p53 under the control of the metallothionein promoter; and collecting virus produced by the cells. In one embodiment the virus is Reovirus, in another the virus is HVT and in a third embodiment the virus is Fowl pox virus.

In yet another aspect of this invention a method is disclosed for propagating virus comprising the steps of: contacting at least one infectious virus particle with a primary cell; growing the primary cells with immortalized cells containing a gene vector expressing p53 under the control of the metallothionein promoter in cell culture; and collecting virus produced from the cell culture.

This invention also relates to immortalized, non-transformed cells containing p53 under the control of the metallothionein promoter and containing at least one vector capable of directing expression of recombinant protein in the cells. In one embodiment the cells express recombinant protein and in another embodiment the vector encodes at least a portion of a recombinant virus. In yet another embodiment the vector is a retroviral vector.

DETAILED DESCRIPTION OF THE INVENTION

Figure 1:
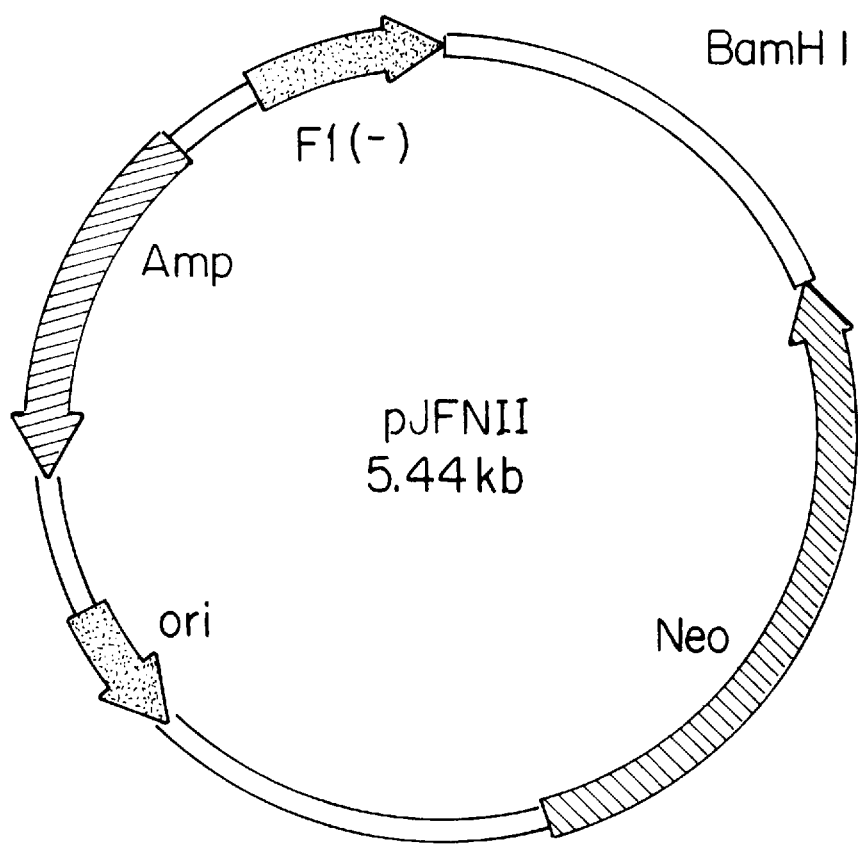
FIG. 1 is a schematic of vector pJFNII, used in a preferred embodiment of this invention.
Figure 2:
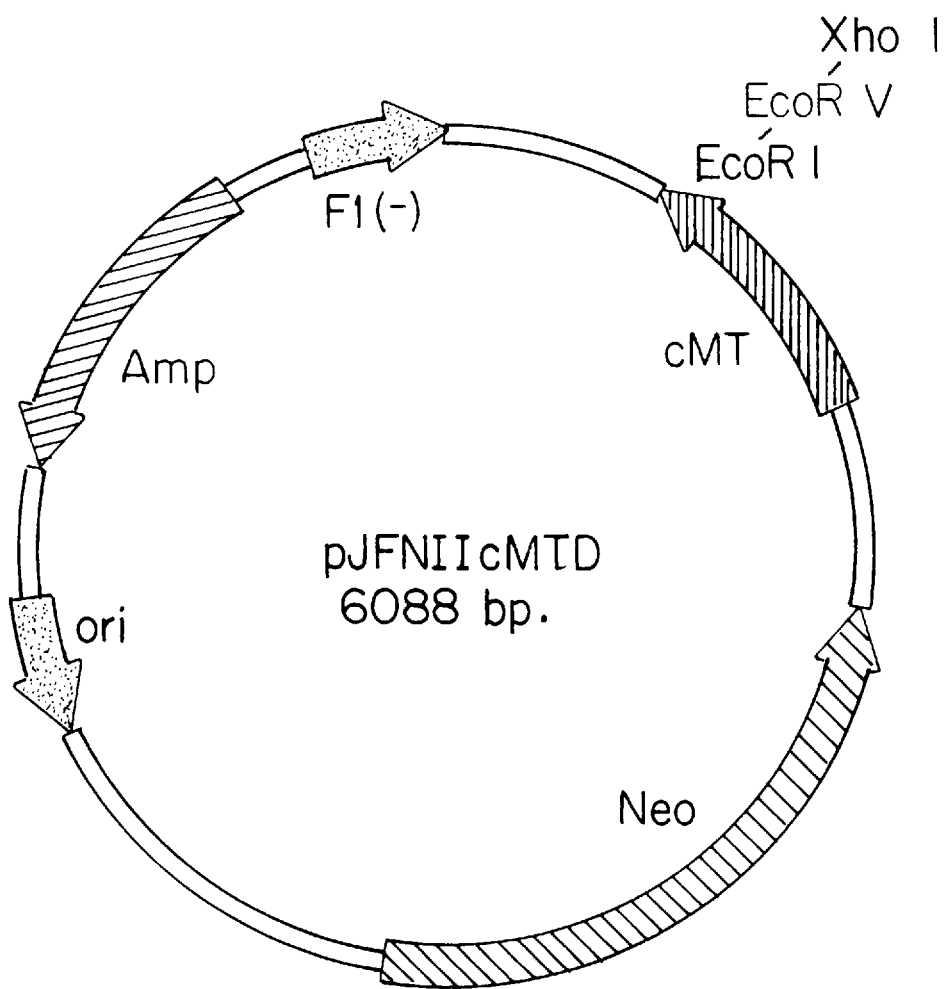
FIG. 2 is a schematic of vector pJFNIIcMTD, used in a preferred embodiment of this invention.

There is a need for a method to reproducibly immortalize primary cells and generate continuous cell lines. The development of technologies to generate well-characterized cell lines that support viral replication will allow companies to save time in repeatedly generating primary cells and obviates the problems associated with the contaminants and inconsistencies that exist between batches of eggs. Defined immortalized cell lines for virus growth reduces costs associated with quality control testing of the final products.

This invention discloses the immortalization of primary non-rodent animal cells, in particular avian and human cells using recombinant p53 under the control of the inducible metallothionein promoter. The cells are useful for growing virus stocks, for expressing virus proteins and as packaging cell lines to produce recombinant virus.

Primary cell cultures are most often derived from freshly isolated cells from intact tissues. These cells are often a good source of virus free material and are well suited as host cells for virus replication. Primary cells are not always efficient at replicating virus and primary animal cells exhibit a limited life span in culture, eventually undergoing senescence. At senescence the cells cease to divide and die out in a matter of time. The ability of cells to divide in culture is dependent on several parameters including the species of origin of the cell and the age of the tissue when it was placed in culture. Cells that undergo senescence cannot be maintained in culture for long periods of time and therefore are not reproducible hosts for the growth of virus stocks. Primary cells generally under go between 23–26 passages before reaching senescence. The cells of this invention are preferably transfected with p53 at about passage 2 to about passage 4.

Immortalized cells, as used throughout this invention, refers to cells capable of growing in culture for greater than 25 passages. Immortalized cells are differentiated from transformed cells in that unlike the transformed cells, the immortalized cells display density dependent growth arrest and maintain a normal morphology. In contrast to immortalized cells, transformed cells are capable of growth in soft agar and are usually able to form tumors when injected into laboratory animals.

The cells of this invention are immortalized by the introduction of p53 under the control of the inducible metallothionein promoter into preferably primary cells. The nuclear oncogene p53 is one of the most well studied tumor suppressor genes in part due to the fact that mutations in the p53 gene contribute in some way to upwards of 50% of all human caners (Levine et al., *Nature* 351:453–456, 1991). p53 is a cellular phosphoprotein and is frequently present at elevated levels in transformed cells (De Leo, A. B. et al. *Proc. Natl. Acad. Sci* 76:2420–2424, 1979). Wild-type p53 appears to function in a growth suppressive manner (Michalovity et al. *Cell* 62:671–680, 1990) and p53 arrests cells at cell cycle checkpoints in response to DNA damage (Kastan, et al. *Cancer Res.* 51:6304–6311, 1991). The checkpoint function is carried out by the accumulation of p53 and a subsequent induction of GADD45 (an important excision repair protein), WAF 1 (p21), and MDM2 (which forms a stable complex with p53) genes. (Kastan, et al. *Cell* 71:587–597, 1992). This theory is supported by the observation that mutations in p53 can result in cellular immortalization.

Several reports link the wild type p53 molecule to inhibition of cell division through a universal inhibitor of cyclin kinases (i.e., Cip1, El-Deiry et al. *Cell* 75:817–825, 1993: WAF1 by Harper et al., *Cell* 75: 805–816, 1993). Experiments show that p53 protein stimulates the production of another protein, p21, which in normal cells is involved in a quartenary complex that includes cyclin-dependent kinase, cyclin, proliferating cell nuclear antigen (PCNA) and p21. In transformed cells the loss of p53 function appears to be due to mutations leading to the loss of p21 and PCNA from the multiprotein complex, resulting in uncontrolled growth.

While mutations in p53 has been associated with the regulation of cellular proliferation, there are other theories postulating other routes for p53 regulation of cell proliferation. (Milner, et al. *Cell Biol. Int. Rep.* 4:663–667, 1980, Milner et al. 112:785–788, 1981, Mercer et al. *Proc. Natl. Acad. Sci.* 79:6309–6312, 1982 and Mercer et al. *Molec. Cell. Biol.* 4:276–281, 1984). For example, mutations in p53 gene may be responsible for negating a cell's ability to repair lesions incurred during critical points in the cell cycle due to physiological and physical parameters such as stress, aging, ionizing irradiation or exposure to carcinogens.

p53 is known in the art to regulate cell proliferation. There is some evidence that nonmutated rat p53 can immortalize rodent cells. Jenkins et al. demonstrated immortalization of rat chondrocytes only when constitutive promoters from tumorigenic viruses such as rous sarcoma virus (RSV) and simian virus 40 (SV40) were used (Jenkins et al. *Nature* 317:816–818, 1985). Eliyahu et al. (*Nature* 312:646–649, 1984) and Parada, et al. (*Nature* 312:649–651, 1984) were also able to immortalize rat cells but their data contradicted Jenkins et al. and demonstrated that p53 constructs failed to immortalize cells when the p53 gene was transfected alone but p53 constructs generated transformed foci when the cells were co-transfected with the oncogene ras. While these cells had characteristics of transformed cells, the cells underwent senescence and stopped multiplying within a relatively short time following transformation.

Unlike Jenkins, Eliyahu, and Parada (all supra), Rovinski and Benchimol (*Oncogene* 2:445–452, 1988) demonstrated immortalization of rat embryo fibroblasts using rat p53 under the control of its endogenous promoter. The results published by Rovinski can be explained by other studies indicating that rat cells are known to readily undergo immortalization and transformation. The cells are believed to be primed in some way so that they are particularly sensitive to immortalization and transformation stimuli. Studies have reproducibly demonstrated that rodent fibroblasts spontaneously immortalize at a high frequency (Ponten, *J. Virol. Monogr.* 8:1, 1971; Ponten J., *Biochim, Biophys. Acta* 458:397, 1976; Todaro and Green *J. Cell Biol.* 17:299–313, 1963; Meek et al., *Exp. Cell Res.* 107:277–284, 1977 and Curatolo, et al. *In Vitro* 20:597–601, 1984). Indeed, Rovinski and Bechimol (supra at page 446) noted that their rat embryo fibroblast controls, transfected with an expression marker alone had a spontaneous frequency of immortalization of about 10%. In contrast, a review in *Science* and other studies indicate that there are no reports of human or chick fibroblasts from normal donors spontaneously immortalizing (Smith et al. *Science* 273:63–67, 1996, Hayflick, *Exp. Cell Res.* 37:614–636, 1965 and Smith et al., *Adv. Cancer Res.* 54:63–77, 1990). Moreover rat cells carry a large variety of endogenous viruses, particularly retroviruses that make them ill-suited for commercial vaccine production.

There are a large number of p53 genes that have been isolated from a variety of mammals. For example the sequence of chicken p53 (SEQ ID NO: 1) is available from GenBank as accession number X 13057 and is available in the literature from Soussi, et al. (*Nucl. Acids Res.* 16(23):11383, 1988). The sequence of normal human p53 is available from GenBank as Accession numbers W88747 and HSP53G and the clone is available to the public through the Washington University School of Medicine. The human p53 gene is also provided as exons 1–11 as GenBank Accession numbers M22881–M22884, M22887–M22888 M22894–M33898 and was published by Buchman, et al. (*Gene* 70(2):245–252, 1988). p53 from the horse is available as GenBank accession number U37120 and from African green monkey (GenBank Accession Number X16384). Rhesus monkey p53 is available as GenBank Accession Number L20442, Cow p53 as X81704 (see also Dequiedt F. et al., *DNA Seq.* 5(4):261–64, 1995), and Cat p53 is available as GenBank Accession Number D26608 (Okuda M. et al. *Int. J Cancer* 58(4):602–7, 1994). Other sequences and publications referencing the use of those sequences can be obtained from a number of gene databases such as GenBank, and the like. Those skilled in the art will be readily able to go to the literature or to gene databases to obtain the gene sequences for p53 that are known in the art.

The metallothionein promoter has a number of metal binding regions and the expression of genes regulated by the metallothionein promoter can be induced by $Cd^{++}$, $Cu^{++}$ and $Zn^{++}$. The promoter contains a number of multiple potential binding sites for metal regulatory factors and for transcription factors including SP1 and MLTF. Metal responsive elements within the promoter regions and other identified regions in the promoter are discussed in detail by Mueller et al. (*Genes & Development* 4:412–426, 1988) and Lee et al. (*Nature* 325:368–372, 1987).

Like the genes encoding p53, there are a number of metallothionein genes from a variety of species that are known in the art. For example, the sequence of the metallothionein promoter from chickens (SEQ ID NO:2) is available in the literature from Fernando, et al. (*Gene.* 8:177–183, 1989). The promoter region can be identified from the metallothionein gene sequence of a number of published metallothionein gene sequences available in the art based on the published characteristics of the metallothionein promoter (Mueller et al., supra and Lee et al., supra). The sequence of the human metallothionein promoter gene is available from GenBank as W68639, X65607, V00594 (see also Stennard et al. *Biochim. Biophys. Acta* 1218(3) :357–365, 1994; Richards et al., *Cell* 37(1):263–272, 1984 and Karin et al., *Nucl. Acids Res.* 10(10):3165–3173, 1982). The metallothionein promoter in sheep is available from GenBank as Accession Number X04626 (see Peterson et al., *Eur. J Biochem.* 160(3):579–585, 1986). Other sequences and publications that reference the use of the sequence can be obtained from a number of gene databases such as GenBank, GenEMBL, and the like. Those skilled in the art will be readily able to go to the literature or to gene databases to obtain the gene sequences for the metallothionein promoters that are known in the art.

The cells of this invention are immortalized through the introduction of nucleic acid encoding p53 into the cells where the nucleic acid encoding p53 is under the control of the metallothionein promoter, that is, the metallothionein promoter is operably linked to nucleic acid encoding p53. In a preferred embodiment of this invention, p53 under the control of the metallothionein promoter is introduced into the cells in an expression vector. There are a variety of commercially available expression vectors and those skilled in the art will be readily appreciate that a variety of vectors can be used to express p53 in a non-rodent animal cell. The expression vector can also include a variety of other features that facilitate replication of the vector in prokaryotic cells, selection of the vector, integration of other gene sequences or facilitate gene expression through the addition of other regulatory sequences. Examples of these features include, but are not limited to the inclusion of a bacterial origin of replication, genes conferring antibiotic resistance, other selectable markers, including but not limited to β-galactosidase, luciferase, or the like, enhancer sequences, multiple cloning sites and the like.

Example 1 details the identification of a metallothionein promoter and a p53 gene along with the incorporation of the promoter and p53 into an expression vector. Preferably the metallothionein promoter and the p53 gene are from the same species. The construct of p53 under the control of the metallothionein promoter was introduced into cells. Preferably the cells are primary cells and primary cells, as used in this disclosure, are preferably cells that have been in culture for 1–10 passages and/or less than 2 months.

Primary cells are generally characterized as cells with a finite ability to grow in culture. Primary cells are those cells isolated from intact tissues and placed in culture. The cells can be obtained from any number of tissues from a variety of species of mammals. Human biopsies, tissue samples from dog, horse, pig, chicken, cow, embryonic tissues, and the like can be minced, digested with trypsin and isolated for transfection as single cells in suspension or as monolayer cultures or as small, but intact, tissue samples. The isolated cells suitable for transfection include fibroblasts, muscle cells, epithelial cells, endothelial cells and others. Those skilled in the art will recognize that there are well known methods for obtaining and isolating a variety of cells from a variety of tissue samples and that these methods can be performed without undue experimentation. Example 2 discloses method for isolating cells from chicken embryonic tissue, including cells from skin, heart muscle and breast muscle.

There are a number of methods known in the art for introducing a vector capable of directing expression of a nucleic acid sequence or for introducing a nucleic acid fragment into cells. These methods include, but are not limited to, $CaPO_4$ precipitation, electroporation, lipofectin transfection techniques, polyamine transfection techniques and transfection with viral particles. Example 3 provides a method for introducing the p53/metallothionein nucleic acid fragments of this invention into eukaryotic cells using lipofectamine. A variety of commercial kits are available that permit nucleic acid fragments to be incorporated into eukaryotic cells using a variety of methods. Therefore, the methods of introduction of the nucleic acid encoding p53 under the control of the metallothionein promoter should not detract from the scope of this invention.

Following transfection, the cells of the invention are grown and expanded under selective growth pressure, if needed, to identify clones containing the transfected nucleic acid fragment. Cells are treated with the necessary cations to promote expression from the metallothionein promoter. Example 3 uses $ZnSO_4$ to induce the metallothionein promoter. Foci of cells are selected and grown in culture. The term "foci" refers to clusters of cells having characteristics that are different from the surrounding cells. In this invention, cells immortalized by the nucleic acid fragment encoding p53 under the control of the metallothionein promoter grow more rapidly than their nonimmortalized counterparts. The immortalized cells grow more rapidly and form clusters on the primary culture monolayers. These clusters can be isolated using cloning rings and expanded in culture.

The cells were considered to be immortalized when they had undergone about 25 tissue culture passages following introduction of the p53/metallothionein containing construct into the cells and when the cells were undergoing at least about 0.6 population doublings per day and preferably between about 0.6 to about 1.5 population doublings per day. The cells maintained a normal morphology and exhibited density dependent and/or contact inhibited growth. Cells from three tissues from chicken embryos were analyzed for their ability to be immortalized by the methods of this invention. A number of clones were identified from heart muscle cells, breast muscle cells and skin cells as provided in Example 5.

The immortalized cells of this invention should be tested for viral contaminants as well as other tissue culture contaminants such as low level bacterial contaminants, mycoplasmas, and the like. The cells can be tested for evidence of retroviral infection, Avian influenza (Type A), Avian reovirus, Avian adenovirus (Groups I–III), Avian encephalomyelitis virus, Fowl pox, Newcastle disease virus, Paramyxovirus (type 2), as well as Mycoplasma, Salmonella and other contaminants such as those listed in 9 C.F.R. § 113 and its subsections.

The cells can be tested for a wide range of viral contaminants using the polymerase chain reaction to identify contaminating nucleic acid fragments. There are a variety of commercially available test kits for a variety of viruses that can be used to determine whether the cells of this invention contain contaminating virus. Similarly, there are commercially available tests to detect viral antigen, wherein the antigen is derived from a variety of different viruses. These tests include ELISA assays, immunofluorescent assays, and the like. All of these assays are well known and involve routine experimental techniques. Example 4 provides a method for determining whether the cells of this invention are reverse transcriptase negative. Evidence of reverse transcriptase activity in the immortalized cells containing p53 under the control of a metallothionein promoter is evidence of retrovirus contamination.

The cells are also tested for their tumorigenic potential. The cells of this invention are preferably not tumorigenic. Tests for determining whether a population of cells is tumorigenic are known in the art. Example 6 provides methods for assessing growth of the immortalized cells of this invention in soft agar and Example 7 provides a method for introducing the cells of this invention into an animal that is preferably species to the cells of this invention to determine whether the cells of the invention are able to induce tumors in the recipient animals. To test the tumorigenic potential of human cells containing nucleic acid encoding p53 under the control of a metallothionein promoter, the cells can be tested for growth in soft agar and tested for growth in nude mice or mice or other laboratory animals with reconstituted human immune systems.

In one aspect of this invention, the cells are useful for propagating virus. The cells of this invention support reovirus infection, Herpesvirus of Turkeys (HVT) and Marek's Disease Virus as demonstrated in Example 8. The cells of this invention derived from chicken tissue can also serve as hosts for Infectious Bursal Disease virus, Infectious Bronchitis Virus, Newcastle Disease Virus, Infectious laryngotrachio virus, a variety of adenoviruses including adenovirus type III, Circodnavirideae, Chicken HSV, fowl pox virus and others. A number of human and animal viruses grow in embryonated eggs including, but not limited to, Rabies virus, Canine Parvovirus, Feline Panleukopenia virus, Calici Virus, Hepatits virus, Influenza viruses, Varicella Zoster Virus and a host of other viruses. These viruses can also be tested for their ability to grow in the immortalized cells of this invention.

To produce virus stock, the cells of this invention can be seeded into tissue culture flasks, roller bottles, spin culture or into hollow fiber reactors. For roller bottle virus propagation, the cells are seeded at about $2-5 \times 10^4$ cells/cm² of surface area. The multiplicity of infection (ratio of infectious virus particles to cells) to initiate virus stock growth will vary depending on virus strain. Those skilled in the art of virology and skilled in the growth of particular viruses and strains of viruses will be able to maximize virus stock yield through the standard manipulation of the multiplicity of infection, temperature, media variations, and the like, without undue experimentation.

Methods for harvesting the virus after infection to obtain infectious virus stock also varies with virus strain. Enveloped viruses egress into the culture media more slowly than non-enveloped virus. Stocks of virus can be obtained from the culture media alone or from cell lysates pooled with the conditioned media. For lytic viruses (those efficient at lysing a cell during virus egress), harvesting the conditioned culture media (e.g., spent media containing virus) after a gentle centrifugation step to remove cell debris is sufficient. Again, methods for harvesting and saving virus from a wide range of virus strains are well known in the art.

There are a variety of methods, also all known in the art, for quantitating virus growth from a culture of cells. For example, the titer of a virus stock for members of the Herpesvirus family and for a variety of viruses producing foci of cytopathology on a cell monolayer surface are readily quantitated by plaque assay (as plaque forming units/ml of culture fluid or as plaque forming units/dose for virus quantitation of vaccine inoculum) or as tissue culture infectious dose—50 ($TCID_{50}$). Rapidly lytic viruses are better quantitated by $TCID_{50}$ as the dose or dilution of virus stock capable of infecting 50% of the cultures in a defined time period. Methods for growing and quantitating virus are known in the art and sources for teaching virus quantification methods are found in Fields, et al. (eds) *Fundamental Virology* 1991, Raven Press, New York or in Mandell, et al. (eds.) *Principles and Practice of Infectious Diseases*, 1985, John Wiley & Sons, New York.

The cells of this invention are also useful for producing recombinant proteins, including viral proteins and the like. Methods for incorporating nucleic acid encoding recombinant protein into a nucleic acid vector under the control of regulatory elements capable of directing expression of a protein in a eukaryotic cell, such as the immortalized cells of this invention, are well known in the art. Expression vectors are replicable nucleic acid fragments that can direct expression of a recombinant protein. Many expression vectors, including retroviral vectors, are available in the art through journal publications and commercial suppliers. Replicable expression vector components generally include, but are not limited to, one or more of the following: an origin of replication, one or more marker genes, enhancer elements, promoter elements, optional signal sequences and transcription termination sequences. The selection or marker genes encode protein that serves to identify a population of transformed or transfected cells. Typical selection genes encode proteins that confer resistance to antibiotics or other toxins, complement auxotrophic deficiencies or supply critical nutrients not available from complex media.

Expression vectors having nucleic acid encoding recombinant protein are transfected into the cells and are used to direct expression of the recombinant protein in the immortalized cells of this invention. The vector preferably can encode any recombinant protein capable of expression in chicken embryonic fibroblast cells, including, but not limited to, virus protein, including reverse transcriptase and/or viral structural protein. Examples of vectors to produce recombinant protein in a cell include retroviral vectors to produce tumor suppressive protein, or viral structural protein such as those disclosed by Givol, et al. *Oncogene* 11(12):2609–2618, 1995, Givol, et al. *Cell Growth & Differentiation* 5(4):419–429, 1994, Federspiel, et al. *Virology* 203(2):211–220, 1994 and Boyer, et al. *Oncogene* 20:457–66, 1993.

The cells of this invention can serve as substrate to express recombinant virus, including, but not limited to recombinant retrovirus. The cells of this invention can serve as packaging cell lines for genetically engineered virus useful for gene therapy, or the like. Constructs and methods for using a particular cell line as a packaging cell line are known in the art. For example, Boerkoel, et al. (*Virology* 195(2):669–79, 1993) discloses methods for packaging virus using primary chicken embryonic fibroblasts as the packaging cell line. These same methods can be used to package virus in the immortalized cells of this invention.

Since most avian cell lines and all transformed avian cells as well as virtually all rodent transformed cell lines either contain viral contaminants such as endogenous virus or produce viral protein, they are not suited for the production of human or animal vaccines. The cells cannot be used to produce recombinant protein because the endogenous contaminants can contaminate purified recombinant protein preparations. Advantageously, the cells of this invention provide a suitable alternative to these problems.

The cells of this invention can also serve as a substrate for supporting virus growth from other cells. These other cells include primary cells, or cultured cells that show improved growth or longevity in culture in the presence of other cells or in the presence of extracellular matrix proteins such as collagens, laminins, and the like. In one embodiment, cells are mixed with virus and then mixed with the cells of this invention preferably in a ratio of cells: to cells of this invention of about between 1:5 cells to about 1:20 cells and more preferably in a ratio of about 1:10 (1 cell to about 10 cells of this invention). The mixed cells are then placed into culture. In a second embodiment the cells are mixed with virus and plated onto the surface of the immortalized cells of this invention are already attached to a tissue culture surface. The cells of this invention serve as a support for the other cells and, without intending to limit the scope of this invention, the cells of this invention can supply growth factors and the like as well as extracellular matrix components, and the like to support the other cells while they are producing virus. Example 9 provides an example of the use of the cells of this invention as a cell substrate.

All references cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully perform the intended invention.

EXAMPLE 1

Preparation of an Exemplary p53 Expression Vector

Plasmid pJFNII (5436 bp) was constructed by starting with the pBluescript SK- vector (Stratagene, LaJolla, Calif.). The multiple cloning site and lacZ gene were removed using PvuII. The 2513 bp vector fragment was treated with calf intestine alkaline phosphatase. The fragment was then treated with EDTA, incubated at 65° C. and extracted with phenol/chloroform followed by ethanol precipitation. The plasmid pRSVneo (Gorman, C., et al. *Science* 221:551–553, 1983) was digested with Bam H1 and Nde I. The fragment was treated with the Klenow fragment of DNA polymerase (Stratagene, LaJolla, Calif.) and blunt-end ligated with the 2513 bp vector fragment. Following isolation of this clone, the vector was digested with EcoRI, treated with Klenow fragment and re-ligated. This digestion removed the EcoRI site from the promoter region. This plasmid was designated pJFNII (see FIG. 1).

pJFNII was cut with BamH1 at a site in the vector about 1000 bp downstream from the SV40 polyadenylation signal used by the gene encoding neomycin resistance. The chicken metallothionein promoter was obtained using PCR. The following primers were used in a polymerase chain reactions (PCR) to obtain the metallothionein promoter: Left primer: 5' CGAAGATCTCTCAGCACGGCCCCACGCT 3' (SEQ ID NO:3) Right Primer: 5' CGAAGATCTTTATTCTC-GAGATATCGAATTCT CGGGTGGGCTCGTAGCAGT 3' (SEQ ID NO:4) In these experiments the template for the PCR reaction was the plasmid pCBcMTlacZ. The chicken metallothionein inducible promoter (Fernando and Andres, *Gene* 81:177–183, 1989) in plasmid pCBcMtlacZ was obtained from Dr. Ann Gibbins (University of Guelph, Guelf, Ontario, Canada). Those skilled in the art will appreciate that the promoter can also be identified from gene expression libraries to obtain the promoter from other species, including chicken. The primers were purchased from IDT (Coralville, Iowa). Both the left and right primers were designed to include BglII sites. Amplification using these primers generated the metallothionein promoter contained within the nucleic acid fragment corresponding to SEQ ID NO:2.

The preferred chicken metallothionein promoter sequence (SEQ ID NO:2) is:

5' CT
CTCAGCACGG CCCCACGCTG TGCGCACCGC CTCGCAGCGC
GGCCCGGGGG GGTGGCGGGG GTGGGAGCAG CAGTGGCGCA
ATGACCCCTC CGGGTCACAT TCCCGCAACC GAGCGCAGAG
TGCGTGGCCG GGAAATTCCC CCCCCCCAAT TCGCCTTTCG
GCAGCCAAAG CGGGAGGGGG GGAGTGAGGA GGGTCAGGCA
CGTTGGGGTC CGTGCCGTGT TCTGGCAAAG TGTCGTGTTT
GGGGGGGGGG GGGAGCAAGG AAGGGAGGCG AGGGGTGAGG
ACACAAAGCA AAAGCGCCCT AAATCTGTTG GCACACATGG
CCATCCCACA GCTGTATCCC CCTGCTTTGG GGGAACCCCA
ACACCAGGGC TGGCCCCGCG GTGAGGCTCC CCCCAGGCAG
GGGGCACGGC CGTGACCCCG CTGAGCACGG CACGGCGCTG
CCCCGCCCCG CTGAGCACGG CACGGCACGG CACGGCACGG
CCCCCCGAGC ACGGCTCAGC ACGGCACGGC GCTCAGCACG
GCACGGATCG GCACCGCCCC GCCGTGCGCT GCGCGCAGCA
CCACCCCGGC CCTATAAATA CAGGGCGGGC AGCGGGACTC
GGGACTGCTA CGAGCCCACC CGAG 3'

This promoter contains three main metal regulatory elements, GC-box regions and a TATA box. The metal regulatory elements bind metal and induce the chicken metallothionein gene positioned down stream. The amplified metallothionein fragment incorporating the BglII termini from the left and right primers was ligated into pJFNII using BamHI. The vector clone identified from this ligation was selected for its ability to confer neomycin resistance. The clone was termed pJFNIIcMTD and was about 6088 bp. The vector included multiple cloning sites including EcoRI, EcoRV and XhoI. A polyadenylation signal within the right primer allowed efficient expression of DNA sequences that lacked this signal.

Chicken p53 cDNA (SEQ ID NO:1) provided as an EcoRI insert from T. Soussi (GenBank Accession # X13057) was incorporated into pJFNIIcMTD at the EcoRI endonuclease restriction site in the multiple cloning site. The cDNA sequence (Soussi et al., *Nucl. Acids Res.* 16:11383, 1988) contains 64 bp of 5' untranslated region (UTR), an open reading frame of 1101 bp encoding a 367 amino acid p53 molecule, a 390 3' UTR and a small poly-A tail. The chicken p53 has about 47% homology to the human homolog. A 1555 bp chicken p53 cDNA containing EcoRI cohesive ends was obtained and the cMT (metallothionein)/SK+ construct was digested with EcoRI. The chicken p53 cDNA insert was ligated into the EcoRI site. Clones containing the p53 insert in the forward (sense) orientation were identified. The construct was transfected into competent E.coli XL-1 Blue cells (Stratagene) and grown in LB broth plus ampicillin overnight. Plasmid was isolated by the maxi-plasmid preparation method of Sambrook, et al. (*Molecular Cloning, A laboratory Manual,* 2nd ed. Cold Spring Harbor, N.Y., 1989). Plasmid DNA was purified twice by $CsCl_2$ centrifugation prior to transfection.

EXAMPLE 2

Isolation of Primary Cells from Intact Tissue

Embryonic SPAFAS line chicken embryos (HyVac, Abel, IA) were the source of the primary cells for these experiments. The eggs and their layers were certified by the supplier as negative for Avian influenza (Type A), Avian reovirus, Avian adenoviruses (Groups I–III), Avian encephalomyelitis virus, Fowl pox, Newcastle disease virus, Paramyxovirus (Type 2), Mycoplasma, Salmonella and other infectious agents known to infect poultry stock. Fertilized eggs were incubated in a sterilized isolated incubator and 10 day old and 19 day old embryos were processed to establish primary cultures.

Three 10 day old SPAFAS embryos were used to obtain cells from the heart, liver, skin and muscle (breast and thigh). A 19 day old embryo was also used to establish primary skin cultures. Embryonic tissue was dissociated using a trypsin/EDTA solution and plated in DMEM media (Gibco) containing 10% fetal calf serum (Gibco). 1% antibiotic/antimycotic (Gibco) containing and 2 mM L-glutamine (Gibco). The dissociated cell suspension was collected in a 50 ml centrifuge tube containing 10% ml fetal bovine serum to inactivate the trypsin and centrifuged at 700xg for 10 minutes.

The cells were resuspended in 10 ml Dulbecco's modified Eagles's medium enriched with 36 $\mu$g/ml insulin (Sigma), 1.6 $\mu$g/ml transferrin (Sigma, St. Louis, Mo.), 2 mM L-glutamine, 10% fetal calf serum, 1% antibiotic/antimycotic solution and pipetted into 4–5 100 $mm^2$ dishes at about $1 \times 10^6$ cells/dish and incubated at 40.5° C. in 5% $CO_2$, 95% air. After 24 hours of incubation, the media was changed.

Cultures were allowed to grow to confluency (5 days) and were removed from the plates using a trypsin/EDTA solution (0.05% trypsin and 0.02% ethylene diamine tetra acetic acid (EDTA) in PBS) and replated for second passage. Cell stocks were frozen in liquid nitrogen.

EXAMPLE 3

Transfection of p53/metallothionein Promoter Construct into Cells

Primary chicken skin cells from ELL-O 19 day embryos were transformed within the first to second passage. The cells were plated at a density of $5 \times 10^5$ cells in 100 $mm^2$ dishes in high glucose DMEM plus 10% certified fetal calf serum and enriched with 1.6 $\mu$g/ml transferrin (Sigma, St. Louis, Mo.), 36 $\mu$g/ml insulin (Sigma) and antibiotics. Cells were grown overnight to stabilize the cultures and refed the next morning with 9 ml of medium and transfected using lipofectamine Transit II using package directions (PanVera Corporation, Madison, Wis.). Each transfection used 10 $\mu$g of the purified p53 construct. Cells were transfected for 5 h and the media was changed using a selectable antibiotic G418 (Sigma, St. Louis, Mo.) at 600 $\mu$g/ml. Transfected cells were passaged in selective medium until foci developed (usually 4–10 days) and the foci were clonally selected and propagated.

Cells were grown for 2–3 passages to generate a foci of G418 (600 $\mu$g/ml) resistant cells (about $10^3$–$10^4$). Cells were initially split when needed at $5 \times 10^5$ cells/100 $mm^2$ dish to avoid influences of plating density on the effects of p53 expression. Nontransfected control cells were sham transfected with a control plasmid. The control cells senesced and died by passage 12. Cells were grown in 50 $\mu$M $ZnSO_4$ selective media for two weeks until stably transfected cells began to proliferate. Several control culture dishes received no zinc sulfate (no induction of the metallothionein promoter). After two weeks of refeeding (four weeks posttransfection) there began to appear phenotypically distinct foci of cells that were growing more rapidly than the surrounding older looking cells. After additional refeedings, one of the foci of the transfected skin cells demonstrated rapidly growing cells. Approximately $5 \times 10^4$ cells/foci were removed from the culture plate using a cloning ring. These cells were transferred to a six well plate. Two dishes of near confluent cells grown in the presence of zinc were split into six dishes at $2 \times 10^5$ cells/dish with the addition of 50 $\mu$M zinc. The skin cells were propagated every 3–4 days in the presence of zinc at $1 \times 10^5$ cells/$cm^2$ until passage 17. There was a drop in population doublings at about passage 20–22 and a later increase back to about 0.7 to about 1.0 population doublings per day. Foci of cells were also obtained from transfected skin cells isolated from 10 day-old chicken embryos. The results of this experiment were surprising because p53 is well known in the literature as a suppressor of tumorigenesis and as a growth regulator. Duplicate cultures of skin cells were transfected with an identical construct containing an anti-sense p53 gene fragment. Cells transfected with this construct did not undergo immortalization.

For primary heart muscle and breast muscle cells, the frozen cultures were thawed and passaged. $8 \times 10^6$ cells (40–70% confluent) of each cell type were transfected with the sense p53 construct with the polyamine compound, lipofectamine Transit II (PanVera Corporation, Madison, Wis.) at passage 2. Non-transfected cells were maintained as a positive growth control and as a negative cell death control (cultures with G418 addition). For transfection, 2–12 $\mu$l/$\mu$g DNA was added dropwise into 100 $\mu$l serum-free medium (RPMI 1640, Life Technologies). The mixture was mixed gently and incubated at room temperature for 5 minutes. 1–3 $\mu$g of DNA was diluted in the Transit II reagent supplied by the manufacturer and incubated for 6 hours. The cells were washed and refed. Following a 24 hr recovery period, both heart and breast cells were split into 4 dishes each at $3 \times 10^5$ cells and placed under G418 selection and zinc induction. Foci of cells were identified in the test cultures. No foci were obtained from control dishes receiving 50 $\mu$M zinc.

EXAMPLE 4

Testing p53-construct Containing Cells for Virus Contaminants

The cells were tested for reverse transcriptase activity. $1 \times 10^6$ cells from rapidly growing cultures were isolated in 4 ml media. The media was taken through several freeze thaws in −80° C. to lyse the cells. The media with lysed cells were layered over a 10% glycerol gradient. The gradient was spun for 60 minutes at 40,000 rpm using an SW40 rotor (Beckman Instruments, Pal Alto, Calif.). Virus particles, if present were pelleted. The media was discarded and the pellet was resuspended in 20 $\mu$l of Nonidet P-40 (Sigma Chemical Co., St. Louis, Mo.).

An eppendorf tube was heated at 41° C. 5 $\mu$l of sample was added to 45 $\mu$l of reverse transcriptase cocktail containing 45 mM Tris, pH 7.8, 2 mM 2-βmercaptothanol, 2 mM manganous acetate, 0.1% Triton X-100, 10 μM each dATP, dCTP, dGTP (Boehringer Mannheim Biochemical, Indianapolis, Ind.), 2.4 μg polyA (Sigma), 60 ng primer dT 12–19 (Pharmacia), 0.4 μCi/reaction $^3$H thymidine triphosphate (15,000 to 28,000 cpm/pmole activity, Amersham).

The reaction was incubated for one hour at 41° C. A negative control used 5 μl of ddH$_2$0 and 45 μl cocktail. Two known positive controls were included with the assay. The assay was stopped by adding 1 ml of 10% trichloroacetic acid (TCA, Columbus Chemical Industries, Inc., Columbus, Wis.). The mixture was filtered through a Whatman GF/C glass 0.45 micron pre filter. Several washes were performed using 5% TCA. The filter was transferred to a scintillation vial containing 5 mls of scintillation counting fluid. Samples were counted on a Beckman Instruments Scintillation counter using a 050 to 600 window setting. An increase of threefold counts over the cocktail background (neg. control) was considered positive.

The primary cultures tested negative as did other cells used in this invention. For further information on reverse transcriptase assays see (Crittenden, et al. *Virology* 57:128–138, 1974).

EXAMPLE 5

Identification of Immortalized Cells

The cells were characterized as immortal when they had undergone more than about 25 passages in tissue culture following the introduction of the p53/metallothionein containing construct into the cells and underwent about 0.6 to about 1.5 population doublings per day. This rate was compared to late stage untreated (i.e., cells that had not received the p53/metallothionein promoter construct) controls that had population doubling rates of about 0.1 to about 0.2 population doublings/day. Skin cells receiving the p53/metallothionein promoter are currently at passage 70 following introduction of the gene construct into the cells. More than twenty immortalized clones were identified in the transfection procedure. The cells were morphologically normal and were contact inhibited. Breast muscle cells are currently at passage 52, are morphologically normal, demonstrate contact inhibited growth and currently have a population doubling rate of about 0.72. Thirteen clones were selected for analysis. The heart cells are currently at passage 20, are morphologically normal, are contact inhibited and have an average population doubling rate of 0.6. Several of the clones have population doubling rates of between about 0.8 and 1.1. More than 10 clones were selected for further study.

EXAMPLE 6

Soft Agarose Colony Formations Assay to Assess Tumorigenic Potential of Cells

To test for tumorigenic potential, the p53/metallothionein promoter transfected cells were tested for growth in soft agar. A soft agarose base was made by mixing 12 ml of a 2% agarose solution (that had been autoclaved and cooled to 56° C.) in 21.6 mls of enriched McCoy's 5A medium [BRL/Gibco, 120 mls fetal calf serum (heat inactivated, 5 mls Na pyruvate(2.2% stock), 1 ml L-serine (21 mg/ml stock), 5 mils L-glutamine (200 mM stock), 12.5 mls Hepes (1 M stock)], 5.9 mls Asparagine (4.4 mg/ml filtered sterilized stock). Seven mls of warm media/agarose was poured onto a 100 mm$^2$ tissue culture dish and allowed to solidify at room temperature in a tissue culture hood for 1 hr.

Cells were removed from actively growing (about 40 to about 70% confluent) cultures by trypsinization to achieve a single cell suspension in fresh DMEM media containing 10% fetal calf serum (with L-glutamine and antibiotics-antimycotic). Approximately 1×10$^6$ cells was added to 4.2 ml of DMEM media containing 10% fetal calf serum, 0.75 ml of 1% agarose, and 50 μl 2β-mercaptoethanol. Care was needed to be certain that the warm media/agarose was at 42° C. before adding the cells. Quickly, 5 ml of the above cell suspension was overlaid on the agarose plates.

Cells were grown at 37° C. in a 5% CO$_2$ and 95% air incubator and observed for 35 days. Duplicate plates were stained with 3 p-nitrophenyl-5-phenyl tetrazolium chlorite (INT stain) and examined at days 0, 5, 10, 15, 20, 30 and 35 for colony formation and growth. All stained colonies greater than 60 μm were considered positive.

All cells tested negative. Further information related to the soft-agar assay is available from Hamburger et al., *Prog. Clin. Biol. Res., Cloning of Human Tumor Stem Cells,* 48, 43–52 (1980); S. Salmon, *Prog. Clin. Biol. Res., Cloning of Human Tumor Stem Cells,* 135–151 (1980); and B. Kressner et al., *Prog. Clin. Biol. Res., Cloning of Human Tumor Stem Cells,* 179–193 (1980).

EXAMPLE 7

Tumorgenicity of Immortalized Cells

Under the guidelines outlined in the University of Minnesota Animal Usage Protocol (protocol #950300-1, March 1995-December 1996) cells were injected into test animals to determine whether or not the cells were tumorigenic. To test the tumorigenic potential of chicken p53 under the control of the chicken metallothionein promoter, the immortalized cells were injected into chickens.

Actively growing cells were removed from cell culture plates and were injected into six SPAFAS line adult chickens. Subcutaneous injections of 4×10$^6$ cells were placed into the wing webs of the chickens. The injection sites were examined weekly for 3.5 months. No tumors were observed at the injection site for any of the transfected cells (skin, heart and muscle) produced to date and all animals remained healthy.

EXAMPLE 8

Virus Propagation in p53/metallothionein Cell Lines

These cells are tested for their ability to support virus production. 2.5×10$^8$ cells containing the p53/metallothionein promoter construct were infected with WSS-Reo 1733 strain of Reovirus having a titer of 8.2 TCID$_{50}$/ml. Cells were infected at a multiplicity of infection of 0.005, 0.001 or 0.0005 infectious virus particles/cell. Infected cells were grown in roller bottles and tested at 48, 64 and 72 hours after infection and demonstrated productive viral growth.

Cells were also seeded in roller bottles at 2.0×10$^4$ cells/cm$^{2.}$ The roller bottles were incubated at 37° C. for 8 days on a roller rack set at 0.4 to 0.5 RPM. Cells were infected with Herpesvirus of Turkeys (HVT virus, strain R2/23). Cells were infected at a multiplicity of infection of 0.001 when there were about 1.33×10$^7$ cells in the roller bottles. Cells were harvested at about 90 to about 96 hours when about 40% of the monolayer had evidence of cytopathology associated with infection. Cells were grown and maintained in DMEM with 10% Hyclone γ-irradiated FBS, 2.5 g/L TPB, 2 mM L-glutamine, 100 U/ml Penicillin, 0.10 mg/ml Streptomycin, 0.25 μg/ml Amphotericin B, 1.6 mg/L insulin and 1.6 mg/L Transferrin. Initial studies demonstrated that the cells produced about $1.4 \times 10^4$ pfu/ml.

Cells were also able to support Marek's Disease Virus replication.

EXPERIMENT 9

Use of Transfected Skin Cells as a Cell Substrate

The cells of this invention are useful as a substrate for supporting virus replication of primary cells. In these experiments the p53 immortalized skin cells are mixed with primary cells. In one study the primary cells are infected and mixed with the immortalized cells and placed in culture and in another study the primary cells are infected and placed onto the immortalized cells where the immortalized cells are already positioned as a lawn in the tissue culture flask. In one example the virus is Egg Drop Syndrome virus and the primary cells are primary chicken embryonic liver cells. In a second example the primary cells are endothelial cells, preferably kidney endothelial cells and the virus is infectious bronchitis virus. The preferred ratio of primary cells to immortalized cells is about 1:5 to about 1:20 and more preferably about 1:10. Virus titers from primary cells growing in the mixed cell population are higher than virus titers from primary cells in culture alone. The immortalized cells allow the primary cells to be used for virus propagation under commercial conditions.

While particular embodiments of the invention have been described in detail, it will be apparent to those skilled in the art that these embodiments are exemplary rather than limiting, and the true scope of the invention is that defined in the following claims.

What is claimed is:

1. A method for transforming chicken cells comprising the steps of:
   positioning nucleic acid encoding p53 under the control of a metallothionein promoter in a gene vector capable of directing expression of p53;
   introducing the gene vector into primary chicken cells; and
   selecting foci of cells with population doubling times of about 0.6 to about 1.5 population doublings per day, wherein the cells are reverse-transcriptase negative and are non-tumorigenic.

2. The method of claim 1, wherein the cells are skin cells.

3. The method of claim 1, wherein the cells are breast muscle cells.

4. The method of claim 1, wherein the cells are heart muscle cells.

5. The method of claim 1, wherein the cells are fibroblasts.

6. A method for propagating virus comprising the steps of:
   contacting at least one infectious virus particle with at least one cell of an immortalized chicken cell culture, wherein the cells of the culture contain a gene vector expressing p53 under the control of the metallothionein promoter; and
   collecting virus produced by the cells.

7. The method of claim 6, wherein the virus is Reovirus.

8. The method of claim 6, wherein the virus is HVT.

9. The method of claim 6, wherein the virus is Fowl pox virus.

10. A method for propagating virus comprising the steps of:
    contacting at least one infectious virus particle with a primary cell;
    growing the primary cells with immortalized chicken cells containing a gene vector expressing p53 under the control of the metallothionein promoter in cell culture; and
    collecting virus produced from the cell culture.

11. Immortalized, non-transformed chicken cells containing p53 under the control of the metallothionein promoter and containing at least one vector capable of directing expression of recombinant protein in the cells.

12. The cells of claim 11 expressing recombinant protein.

13. The cells of claim 12 wherein the vector encodes at least a portion of a recombinant virus.

14. The cells of claim 11 wherein the vector is a retroviral vector.

* * * * *